United States Patent
Kim et al.

(10) Patent No.: US 11,510,853 B2
(45) Date of Patent: *Nov. 29, 2022

(54) COMPOSITION FOR SKIN SOOTHING CONTAINING LIQUID-PHASE PLASMA

(71) Applicant: AJOU UNIVERSITY INDUSTRY-ACADEMIC COOPERATION FOUNDATION, Suwon-si (KR)

(72) Inventors: Chul Ho Kim, Seoul (KR); Kyoungwon Jung, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/648,087

(22) PCT Filed: Sep. 17, 2018

(86) PCT No.: PCT/KR2018/010941
§ 371 (c)(1),
(2) Date: Mar. 17, 2020

(87) PCT Pub. No.: WO2019/054836
PCT Pub. Date: Mar. 21, 2019

(65) Prior Publication Data
US 2020/0261325 A1    Aug. 20, 2020

(30) Foreign Application Priority Data
Sep. 18, 2017  (KR) ........................ 10-2017-0119293

(51) Int. Cl.
*A61K 8/02*    (2006.01)
*A61K 8/19*    (2006.01)
(Continued)

(52) U.S. Cl.
CPC .............. *A61K 8/0204* (2013.01); *A61K 8/19* (2013.01); *A61Q 17/04* (2013.01); *A61Q 19/08* (2013.01)

(58) Field of Classification Search
CPC .. A61K 8/0204; A61K 8/19; A61K 2800/522; A61K 8/02; A61K 2800/83; A61K 2800/22; A61Q 17/04; A61Q 19/08
See application file for complete search history.

(56) References Cited

U.S. PATENT DOCUMENTS 1,546,476 A    7/1925 Crockett
3,951,218 A    4/1976 Sjogren
(Continued)

FOREIGN PATENT DOCUMENTS

JP    10-286316 A    10/1998
JP    2014-212839 A    11/2014
(Continued)

OTHER PUBLICATIONS

International Search Report for PCT/KR2018/010941, dated Mar. 22, 2019.
(Continued)

*Primary Examiner* — Carlos A Azpuru
(74) *Attorney, Agent, or Firm* — Sughrue Mion, PLLC (57) ABSTRACT

The present invention is to provide a composition for skin soothing, which is safe from a risk of side effects, and relates to a composition for skin soothing containing a liquid-phase plasma. The liquid-phase plasma of the present invention is obtained by applying plasma as pure energy to a liquid-phase material, and can be used in the skin sensitive to a chemical material without a risk of side effects. Furthermore, the liquid-phase plasma has remarkable effects on the prevention or treatment of dermatitis or photo-aging due to (Continued)

ultraviolet light, and thus is expected to be greatly used in beauty care and mechanical fields.

2 Claims, 6 Drawing Sheets

(51) Int. Cl.
 *A61Q 17/04* (2006.01)
 *A61Q 19/08* (2006.01)

(56) References Cited

U.S. PATENT DOCUMENTS

| | | | |
|---|---|---|---|
| 4,974,487 | A | 12/1990 | Goldstein et al. |
| 5,876,663 | A | 3/1999 | Laroussi |
| 6,150,755 | A | 11/2000 | Druz et al. |
| 6,518,538 | B2 | 2/2003 | Bernabei |
| 7,192,553 | B2 | 3/2007 | Crowe et al. |
| 7,368,542 | B2 | 5/2008 | McIntyre |
| 7,812,307 | B2 | 10/2010 | Dutton et al. |
| 9,067,273 | B1 | 6/2015 | Kim et al. |
| 9,169,317 | B2 | 10/2015 | McIntyre |
| 9,226,790 | B2 | 1/2016 | Zemel et al. |
| 9,255,330 | B2 | 2/2016 | Vangeneugden et al. |
| 9,288,886 | B2 | 3/2016 | Koo et al. |
| 9,363,880 | B2 | 6/2016 | Keener et al. |
| 9,750,951 | B2 | 9/2017 | Kim et al. |
| 9,861,829 | B2 | 1/2018 | Jacofsky et al. |
| 10,039,927 | B2 | 8/2018 | Watson et al. |
| 10,493,263 | B2 | 12/2019 | Roe et al. |
| 10,524,848 | B2 | 1/2020 | Sartor |
| 10,537,014 | B2 * | 1/2020 | Kim ..................... A61K 9/0031 |
| 11,102,877 | B2 | 8/2021 | Eckert et al. |
| 11,167,146 | B2 | 11/2021 | Canady et al. |
| 2002/0187066 | A1 | 12/2002 | Yu et al. |
| 2005/0101016 | A1 | 5/2005 | McIntyre |
| 2006/0278254 | A1 | 12/2006 | Jackson |
| 2007/0213700 | A1 | 9/2007 | Davison et al. |
| 2008/0119781 | A1 | 5/2008 | King |
| 2012/0089084 | A1 * | 4/2012 | O'Keeffe ............ A61L 26/0033 604/24 |
| 2012/0094250 | A1 | 4/2012 | Lloyd et al. |
| 2013/0109838 | A1 | 5/2013 | McIntyre |
| 2013/0345620 | A1 * | 12/2013 | Zemel ................. A61B 18/042 604/24 |
| 2014/0377320 | A1 | 12/2014 | Pietramaggiori et al. |
| 2015/0352516 | A1 | 12/2015 | Imada et al. |
| 2015/0366042 | A1 | 12/2015 | Zaidi |
| 2016/0296763 | A1 | 10/2016 | Kim et al. |
| 2017/0189349 | A1 | 7/2017 | Roe et al. |
| 2017/0354616 | A1 | 12/2017 | Roe et al. |
| 2017/0354815 | A1 | 12/2017 | Roe et al. |
| 2019/0313520 | A1 | 10/2019 | Kim et al. |
| 2020/0129386 | A1 | 4/2020 | Kim et al. |
| 2020/0179709 | A1 | 6/2020 | Kim et al. |
| 2020/0254008 | A1 | 8/2020 | Kim et al. |

FOREIGN PATENT DOCUMENTS

| | | |
|---|---|---|
| JP | 2015-084290 A | 4/2015 |
| KR | 10-0479741 B1 | 3/2005 |
| KR | 10-0509848 B1 | 8/2005 |
| KR | 10-2008-0004452 A | 1/2008 |
| KR | 10-1101321 B1 | 1/2012 |
| KR | 10-2012-0039199 A | 4/2012 |
| KR | 10-1248668 B1 | 3/2013 |
| KR | 10-2013-0099522 A | 9/2013 |
| KR | 10-1409390 B1 | 6/2014 |
| KR | 10-2015-0065147 A | 6/2015 |
| KR | 10-2015-0084146 A | 7/2015 |
| KR | 10-1568380 B1 | 11/2015 |
| KR | 10-1577207 B1 | 12/2015 |
| KR | 10-1635718 B1 | 7/2016 |
| KR | 10-1657063 B1 | 9/2016 |
| KR | 10-2016-0124316 A | 10/2016 |
| WO | 2005/125286 A2 | 12/2005 |
| WO | 2015/191843 A1 | 12/2015 |
| WO | 2016-096751 * | 6/2016 |
| WO | 2016/096751 A1 | 6/2016 |
| WO | 2016/167516 A1 | 10/2016 |

OTHER PUBLICATIONS

International Search Report dated Feb. 19, 2018 in International Application No. PCT/KR2017/010234.
Brun et al., "Adipocyte differentiation: a transcriptional regulatory cascade", Current Opinion in Cell Biology, 1996, vol. 8, pp. 826-832 (7 pages total).
Darlington et al., "The Role of C/EBP Genes in Adipocyte Differentiation", The Journal of Biological Chemistry, 1998, vol. 273, No. 46, pp. 30057-30060 (4 pages total).
Jessen et al., "Expression profiling during adipocyte differentiation of 3T3-L1 fibroblasts", Gene, 2002, vol. 299, pp. 95-100 (6 pages total).
Osborne, "Sterol Regulatory Element-binding Proteins (SREBPs): Key Regulators of Nutritional Homeostasis and Insulin Action", The Journal of Biological Chemistry, 2000, vol. 275, No. 42, pp. 32379-32382 (5 pages total).
Rosen et al., "Molecular Regulation of Adipogenesis", Annu. Rev. Cell Dev. Biol., 2000, vol. 16, pp. 145-171 (33 pages total).
Steppan et al., "Resistin and obesity-associated insulin resistance", TRENDS in Endocrinology & Metabolism, 2002, vol. 13, No. 1, pp. 18-23 (6 pages total).
Tontonoz et al., "mPPARy2: tissue-specific regulator of an adipocyte enhancer", Genes & Development, 1994, vol. 8, pp. 1224-1234 (12 pages total).
Spiegelman et al., "Adipogenesis and Obesity: Rounding Out the Big Picture", Cell, 1996, vol. 87, pp. 377-389 (13 pages total).
International Search Report dated Feb. 19, 2018 in International Application No. PCT/KR2017/010235.
Abbas et al., "Cellular and Molecular Immunology", Section V—Immunity in Defense and Disease, pp. 456, Table 19-4 (1 page total).
Kang et al., "N2 non-thermal atmospheric pressure plasma promotes wound healing in vitro and in vivo Potential modulation of adhesion molecules and matrix metalloproteinase-9", Experimental Dermatology, 2017, vol. 26, pp. 163-170 (8 pages total).
Lee et al., "Nonthermal Plasma Induces Apoptosis in ATC Cells: Involvement of JNK and p38 MAPK-Dependent ROS", Yonsei Med J, 2014, vol. 55, No. 6, pp. 1640-1647 (8 pages total).
Kubinova et al., "Non-thermal Air Plasma Promotes the Healing of Acute Skin Wounds in Rats", Sci Rep, 2017, vol. 7, No. 45183 (11 pages total).
Lee et al., "Suppression of scar formation in a murine burn wound model by the application of nonthermal plasma", Appl. Phys. Lett., 2011, vol. 99, No. 203701 (4 pages total).
Sato et al., "Successful Use of Argon Plasma Coagulation and Tranilast to Treat Granulation Tissue Obstructing the Airway After Tracheal Anastomosis", Chest, 2000, vol. 118, No. 6, pp. 1829-1831 (3 pages total).
Sharma et a., "Effects of Cold Atmospheric Pressure Plasma Jet on the Viability of Bacillus subtilis Endospores", 2013, gair.media.gurima-u.ac.jp/dspace/bitstream/10087/7661/1lThesis%2ofor%2oDoctor%200f%2oEngineering%20(VinitaSharma).pdf Year: 2013 (129 pages total).
Mohades et al., "Temporal evaluation of the anti-tumor efficiency of plasma-activated media", Plasma Process Polym., 2016, vol. 13, pp. 1206-1211 (6 pages total).
International Search Report dated Feb. 8, 2018 in International Application No. PCT/KR2017/012771.

* cited by examiner

COMPOSITION FOR SKIN SOOTHING CONTAINING LIQUID-PHASE PLASMA

GOVERNMENT SUPPORT This invention was made, at least in part, with government support under Grant Identification No. HR21C1003 (1465034377) awarded by the Ministry of Health and Welfare of Republic of Korea.

CROSS REFERENCE TO RELATED APPLICATIONS

This application is a National Stage of International Application No. PCT/KR2018/010941 filed Sep. 17, 2018, claiming priority based on Korean Patent Application No. 10-2017-0119293 filed Sep. 18, 2017.

TECHNICAL FIELD

The present invention relates to a skin soothing composition including a liquid-type plasma. More particularly, the present invention relates to a skin soothing composition, which includes a "liquid-type plasma" prepared by generating a high-density high-energy plasma in a liquid as an active ingredient, and a method of preparing the same.

BACKGROUND ART

Skin aging includes natural aging that occurs over time and aging caused by the external environment. In terms of skin aging, the most important element of the external environment is sunlight, and aging caused thereby is specifically called photoaging. Among the sunlight, the rays that damage the skin are ultraviolet (UV) rays, and UV-B with short wavelengths (280 to 320 nm), which are known to be the major cause of skin damage. When exposed repeatedly to UV rays for a long time, the skin shows changes such as lost elasticity, wrinkles, roughness, and age spots (J. Invest Dermatol. m 1979, 73; 47~53). In photoaged skin, the epidermis thickens, a large amount of abnormal elastin accumulates in the upper dermis, dermal collagen is progressively lost and degraded, and mucopolysaccharides increase. In addition, mast cells increase, and inflammatory responses, such as an increase in the number of white blood cells in tissue, also occur (J. Am. Acad. Dermatol., 1989; 610~613 and Photochem. Photobiol., 1995; 62; 348~352).

Recently, as interest in beauty increases, medical or cosmetic compositions for preventing photoaging have been actively studied. However, since most compositions relate to the discovery or combination of novel chemicals, there is a problem of acting as irritants to sensitive skin. As one example, although hydroxy acids and retinoids were proven to induce improvements in appearance, skin glow or the treatment of age spots for photodamaged or naturally aged skin, it is known that, when these components are applied at high concentration, sometimes, there are side effects such as skin irritation, for example, skin redness and a stinging sensation in application.

Accordingly, the present invention is to provide a composition for soothing skin which is safe from the risk of side effects, and relates to a composition for soothing dermatitis induced by UV rays including a liquid-type plasma. The liquid-type plasma of the present invention is prepared by irradiating a plasma as pure energy to a liquid-phase material, and since it can be used on skin sensitive to a chemical without side effects, and has a significant effect in prevention or treatment of dermatitis or photoaging caused by UV rays, it is expected to be widely used in cosmetic and medical fields.

DISCLOSURE

Technical Problem

The present invention has been conceived to solve the above-described conventional technical problems, and relates to a composition for soothing skin, which includes a liquid-type plasma.

However, technical problems to be solved in the present invention are not limited to the above-described problems, and other problems which are not described herein will be fully understood by those of ordinary skill in the art from the following descriptions.

Technical Solution

Hereinafter, the present invention will be described with reference to various embodiments. In the following description, for full understanding of the present invention, various specific details, for example, specific forms, compositions and processes will be described. However, certain embodiments may be implemented without one or more of the specific details, or in combination with other known methods and forms. In another example, known processes and manufacturing techniques are not described in particular detail so as to not unnecessarily obscure the present invention. Throughout the specification, the reference to "one embodiment" or "embodiment" means that a specific feature, form, composition or property described in conjunction with the embodiment is included in one or more embodiments of the present invention. Therefore, the context of the "one embodiment" or "embodiment" expressed in various locations throughout the specification does not necessarily represent the same embodiment of the present invention. In addition, a specific feature, form, composition or property may be combined by any suitable manner in one or more embodiments.

The "photoaging" used herein refers to skin aging symptoms caused by long-term exposure of the skin to sunlight. Particularly, photoaging is known to account for 80% of facial aging. The skin is affected by "UV rays" in sunlight, which stimulates skin aging by reducing collagen synthesis and increasing collagen degradation. Among ultraviolet rays, "UV-B" in the wavelength range of 280 to 320 nm is known to have a sunburn-causing ability approximately 1,000 times stronger than "UV-A" of 320 to 400 nm. UV-A is relatively weak compared to UV B, but is still involved in skin erythema. Particularly, as time goes to the time zone (between the noon and 2 pm) in which the surface angle of the sun increases, an amount of UV B decreases and UV-A increases, which gradually affects skin redness caused by sunlight. When the skin is exposed to LTV rays for a long time, photoaging disrupts the balance of an antioxidant system in cells or tissue, resulting in oxidative stress. Clinical symptoms of photoaging include an increase in wrinkles, an increase in skin pigmentation such as chloasma, freckles or age spots, increased skin dryness, or a decrease in skin elasticity, and photoaging is uncommonly developed to a tumor (melanoma).

In one embodiment of the present invention, the "non-thermal atmospheric pressure plasma" is also called a cold or non-equilibrium plasma, which is an opposite concept of a thermal plasma. The non-thermal atmospheric pressure plasma may be easily made with low enemy under a relatively low pressure, and although the temperature of a reaction gas for the non-thermal atmospheric pressure plasma is similar to an atmospheric temperature, only an electron temperature is approximately 10 to 100 times higher than the temperature of the reaction gas. The non-thermal atmospheric pressure plasma under an atmospheric or high pressure generates a reactant having very high chemical reactivity, and thus has a characteristic of promoting a chemical reaction that is difficult to be realized or impossible to be performed by a general method. In the present invention, the plasma generator may be any one that can generate a non-thermal atmospheric pressure plasma without particular limitation. A carrier gas used for the generation of the non-thermal atmospheric pressure plasma is preferably any one or more selected from the group consisting of oxygen, nitrogen, helium, and argon, and more preferably nitrogen, but the present invention is not limited thereto.

In one embodiment of the present invention, the "liquid-type plasma (LTP)" refers to a high-density high-energy plasma generated in a liquid, and may be prepared by exposure to an atmospheric-pressure room-temperature non-thermal plasma (NTP). The term "liquid-type plasma (LTP)" may be interchangeably used with the term "plasma-conditioned liquid material", and the "liquid-phase material" is any liquid-type material without limitation, and preferably, water, saline, a buffer or a culture medium, and most preferably, a culture medium.

Since the LTP of the present invention can be provided in the form of a liquid composition, it is convenient to commercially distribute and carry, and it is possible to provide moisturizing and treatment at the same time in skin diseases in which moisturizing is important. In addition, the liquid plasma has less cell damage than direct plasma treatment of an affected area, has no risk of skin damage such as a burn caused by erroneous operation of a device, and is able to be uniformly applied in a wide curved area.

In one embodiment of the present invention, the "culture medium" refers to a medium capable of supporting cell growth and survival in vitro, and includes all of conventional media used in the field suitable for cell culture. Media and culture conditions may be selected depending on the type of cells. A basal medium used in cell culture is preferably a cell culture minimum medium (CCMM), which generally includes a carbon source, a nitrogen source and trace elements. Such a basal medium for cell culture may be, for example, Dulbecco's Modified Eagle's Medium (DMEM), Minimal Essential Medium (MEM), Basal Medium Eagle (BME), RPMI1640, F-10, F-12, Glasgow's Minimum Essential Medium (GMEM) or Iscove's Modified Dulbecco's Medium, but the present invention is not limited thereto.

In one embodiment of the present invention, the "treatment" refers to all actions involved in alleviating or beneficially changing photoaging or symptoms of diseases caused thereby using the LTP according to the present invention. Those of ordinary skill in the art to which the present invention belongs can determine exact criteria for photoaging, and the degree of improvement, enhancement and treatment of photoaging with reference to the materials presented by the Korean Medical Association, etc.

In one embodiment of the present invention, the "prevention" refers to all actions of inhibiting or delaying photoaging or other diseases caused thereby using the LTP of the present invention. It will be obvious to those of ordinary skill in the art that the composition of the present invention having a therapeutic effect on photoaging can prevent the disease using the LTP according to the present invention when an early symptom is shown or before symptoms are shown.

The "pharmaceutical composition" used herein refers to a composition administered for a specific purpose. In terms of the object of the present invention, the pharmaceutical composition of the present invention includes LTP prepared by irradiating a liquid-phase material with a plasma as an active ingredient, and may include a protein involved therein and a pharmaceutically acceptable carrier, excipient or diluent. The "pharmaceutically acceptable" carrier or excipient has been approved by a regulatory department of the government, or listed in the government- or other generally approved pharmacopoeia for use in vertebrates, and more particularly, humans.

A pharmaceutical composition of the present invention for parenteral administration may be prepared as a suspension, solution or emulsion contained in an oily or aqueous carrier, or prepared as a solid or semi-solid. In addition, the pharmaceutical composition of the present invention may include a formulation agent such as a suspending agent, a stabilizer, a solvent and/or a dispersant, and may be sterilized. The pharmaceutical composition may be stable under preparation and storage conditions, and may be preserved from contamination by microorganisms such as bacteria or fungi. Alternatively, the pharmaceutical composition of the present invention may be prepared as a sterilized powder for reconstitution with a suitable carrier before use. The pharmaceutical composition may be present in a unit-dose form, such as a microneedle patch, an ampoule, or other unit-dose containers, or in a multiple-dose container. Alternatively, the pharmaceutical composition may be stored in a freeze-dried (lyophilized) state, which requires only the addition of a sterilized liquid carrier, for example, water for injection immediately prior to use. An injection solution and a suspension may be immediately prepared from sterile powder, granules or tablets.

In some non-limiting embodiments, the pharmaceutical composition of the present invention may be formulated, or may be included in the form of a microparticle in a liquid. In some non-limiting embodiments, the pharmaceutical composition of the present invention may include a pharmaceutically acceptable compound and/or mixture at a concentration ranging from 0.001 to 100,000 U/kg. In some non-limiting embodiments, in the pharmaceutical composition of the present invention, suitable excipients may include a preservative, a suspending agent, an additional stabilizer, a color, a buffer, an antibacterial agent, an antifungal agent, and an isotonic agent such as sugar or sodium chloride. The term "stabilizer" used herein refers to a compound selectively used in the pharmaceutical composition of the present invention to increase a shelf life. In a non-limiting embodiment, the stabilizer may be a saccharide, an amino acid or a polymer. In addition, the pharmaceutical composition of the present invention may include one or more pharmaceutically acceptable carriers, and the carrier may be a solvent or dispersion medium. Non-limiting examples of the pharmaceutically acceptable carriers include water, saline, ethanol, polyols (e.g., glycerol, propylene glycol and liquid polyethylene glycol), oils, and a suitable mixture thereof. The non-limiting examples of sterilization techniques applied to the pharmaceutical composition of the present invention include filtration through a bacteria-inhibiting filter, terminal sterilization, incorporation with a sterile preparation, irradiation, sterile gas injection, heating, vacuum drying and freeze drying.

The "administration" used herein refers to introduction of the composition of the present invention to a patient by any suitable method, and the composition of the present invention may be administered by any general route as long as it can reach the desired tissue. While the administration may be oral, intraperitoneal, intravenous, muscular, subcutaneous, intradermal, intranasal, intrapulmonary, intrarectal, intrathecal or intradural administration, the pharmaceutical composition of the present invention is most preferably applied to the skin or provided by subcutaneous or intradermal injection, but the present invention is not limited thereto.

The treatment method of the present invention may include administration of the pharmaceutical composition at a pharmaceutically effective amount. In the present invention, the effective amount may be adjusted according to various parameters including the type and severity of a disease, the type and content of the active ingredient and other components contained in the composition, the type of dosage form, and the age, body weight, general health condition, gender and diet of a patient, administration time, administration route, a release rate of the composition, a treatment period, and a co-administered drug.

In one embodiment of the present invention, a method of preparing LTP for soothing skin, which includes (a) filling a plasma generator with a carrier gas; (b) generating a plasma by providing a voltage of 1 kV to 30 kV and a frequency of 10 to 30 kHz to the plasma generator; and (c) irradiating a liquid-phase material with the generated plasma, is provided. The carrier gas in Step (a) is any one or more selected from the group consisting of nitrogen, helium, argon, and oxygen, and preferably nitrogen, the irradiation in Step (c) is performed for 10 to 120 seconds per mL at a distance of 0.1 to 15 cm from the surface of the liquid-phase material, the liquid-phase material in Step (c) is water, saline, a buffer or a culture medium, and the soothing skin means soothing of UV-damaged skin.

In Step (b), a plasma is preferably generated by providing a voltage of 1 to 30 kV and a frequency of 10 to 30 kHz, and outside the above ranges, a problem of cytotoxicity or reduced effects may occur.

In addition, the irradiation in Step (c) is preferably performed for 10 to 120 seconds per mL at a distance of 0.1 to 15 cm from the surface of the liquid-phase material, and outside the ranges, the effects may be insignificant.

In another embodiment of the present invention, a cosmetic composition for soothing skin, which includes LTP prepared by any one or more of the above-described methods, is provided.

In still another embodiment of the present invention, a pharmaceutical composition for preventing or improving photoaging, which includes LTP prepared by any one or more of the above-described methods, is provided.

In yet another embodiment of the present invention, a pharmaceutical composition for preventing or treating skin damage caused by UV rays, which includes LTP prepared by any one or more of the above-described methods, is provided, wherein the skin damage is any one selected from the group consisting of dermatitis, skin wrinkles, xeroderma, reduced skin elasticity, increased skin keratin, erythema, milia, chloasma, freckles, age spots, and melanoma.

Hereinafter, the present invention will be described in detail step by step.

Advantageous Effects

The present invention relates to a skin soothing composition, including a liquid-type plasma (LTP), wherein the LTP of the present invention can be used for skin sensitive to a chemical without a risk of side effects and have a significant effect of preventing or treating dermatitis or photoaging caused by UV rays, and therefore the LTP is expected to be widely used in cosmetic and medical fields.

MODES OF THE INVENTION

Hereinafter, the present invention will be described in further detail with reference to examples. These examples are merely provided to illustrate the present invention, and it should be obvious to those of ordinary skill in the art that the scope of the present invention is not limited by the following examples according to the gist of the present invention.

Example 1

Preparation of Liquid Plasma

A liquid-type plasma (LTP) was prepared using an atmospheric plasma generator equipped with a quartz or ceramic tube as a dielectric and including a multi-nozzle non-thermal plasma source. The generator was designed to have a gas supply nozzle diameter of less than 3 mm, and to generate a uniform plasma having a 1-inch size for medical research. The LTP was prepared by a method of supplying nitrogen ($N_2$) as a carrier gas to the generator at a flow rate of 10 L/min, and applying the plasma for 60 seconds per mL at a distance of 4 cm from the bottom surface of a culture dish (12-well plate, TPP, Renner, Dannstadt, Germany) into which Dulbecco's Modified Eagle Medium (DMEM) was dispensed. Here, the power supply specifications of the plasma generator preferably are a voltage of 1 to 30 kV and an average frequency of 10 to 30 kHz, and most preferably, a voltage of 15 kV and an operation frequency of 15 kHz, but the present invention was not limited thereto.

Example 2

UV Treatment for Immortalized Human Keratinocyte Cell Line

An immortalized human keratinocyte (HaCaT) cell line was provided from the Korean Cell Line Bank, and cultured in DMEM containing 10 vol % FBS and 1 vol % antibiotic/antibacterial agent.

For UV treatment, $1\times10^6$ of the HaCaT cells were seeded in a 100-mm plate, after 24 hours, the cells were washed with phosphate-buffered saline (PBS), and the medium was replaced with a 1% FBS-containing medium. After 24 hours, the cells were irradiated with 20 mJ/cm$^2$ or 100 mJ/cm$^2$ UVB (280-320 nm) in a minimal amount of PBS (~2 ml), immediately after the irradiation, incubated in DMEM for 15 minutes, and collected for Western blotting. For an LTP experimental group, 1 hour prior to the UVB irradiation, cells were pretreated with LTP for 1 hour, and immediately after the UVB irradiation, incubated with LTP, instead of DMEM, for 15 minutes.

Example 3

Confirmation of LTP (Nitrogen Plasma) Effect on UV-Damaged Epidermal Cells

Figure 1:
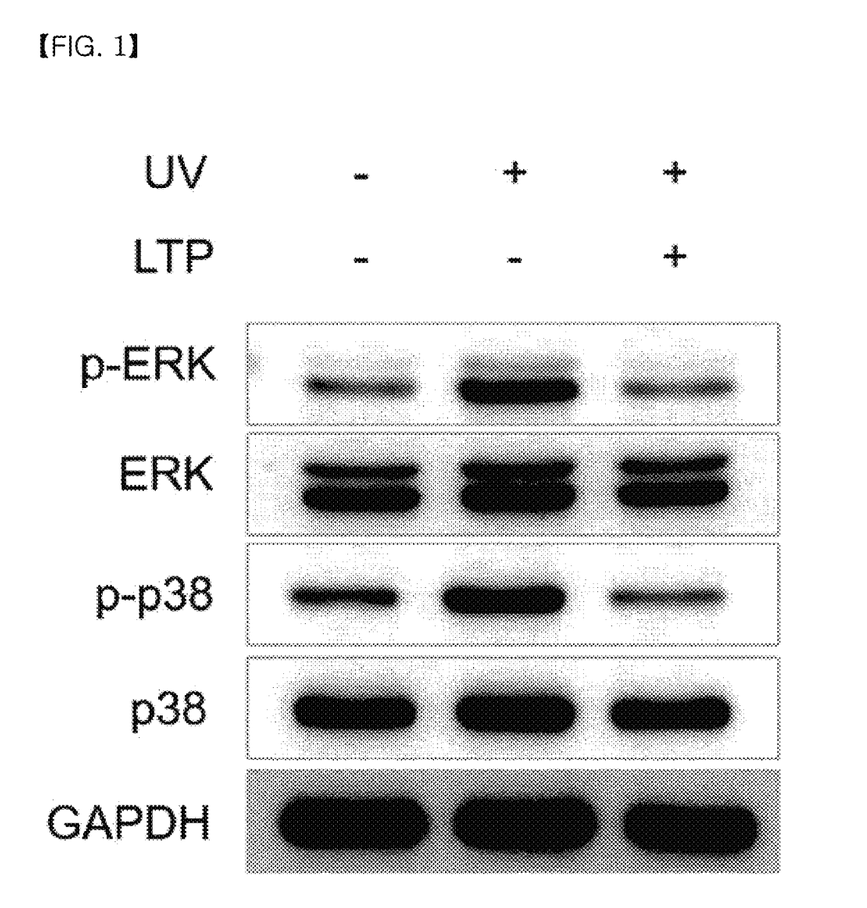
FIG. 1 shows the result of confirming the activity of ERK and p38 in epidermal cells treated with a liquid-type plasma (LTP) before and after UV stimulation according to an example of the present invention.
Figure 2:
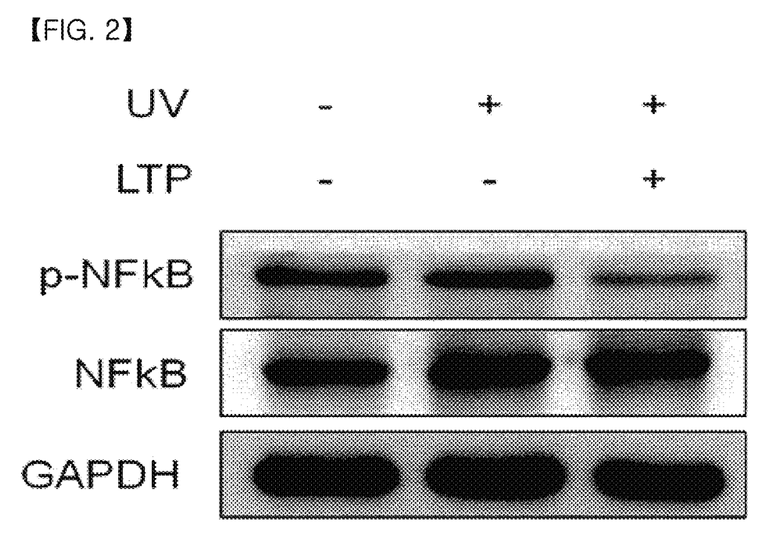
FIG. 2 shows the result of confirming the activity of NF-kB in epidermal cells treated with LTP before and after UV stimulation according to an example of the present invention.
Figure 3:
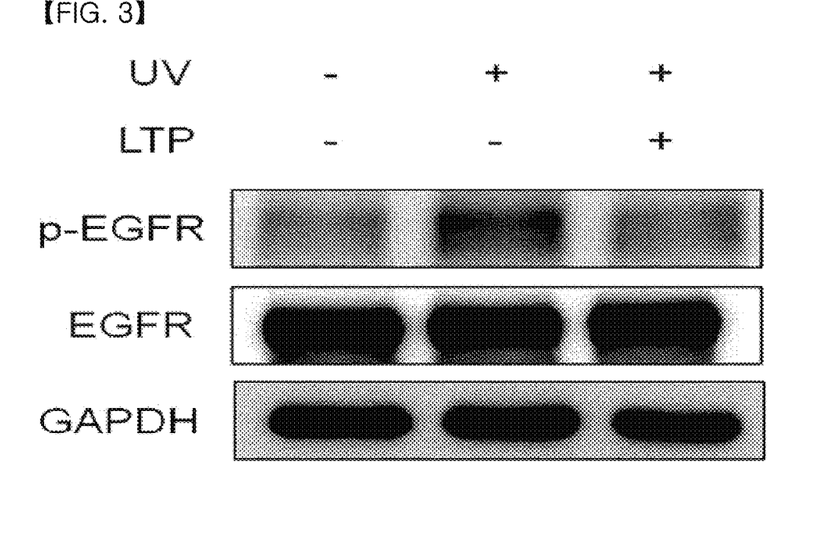
FIG. 3 shows the result of confirming the activity of EGFR in epidermal cells treated with LTP before and after UV stimulation according to an example of the present invention.

Cells further cultured for 15 minutes after treatment with 20 mJ/cm$^2$ UV rays were lysed with a RIPA buffer (150 mM NaCl, 1.0% Nonidet-P 40, 0.5% sodium deoxycholate, 0.1% sodium dodecyl sulfate, 50 mM Tris, pH 8.0, and a protease inhibitor cocktail, and PhoSTOP (Roche Molecular Biochemicals, Basel, Switzerland)), 10 µg of a protein lysate was loaded in a 10% SDS/PAGE gel to isolate proteins, and then proteins were transferred to a PVDF membrane (Amersham, Arlington Heights, Ill., USA). The protein-transferred PVDF membrane was reacted with a pERK, ERK, p-p38, p38, p-NFκB, NFκB, p-EGFR, EGFR or GAPDH (Cell Signaling Technology) antibody, the extent of the expression of each signal was measured with ECL Western blotting detection reagents (Amersham). The expression level of each signal was recalculated based on a GAPDH signal. The results are shown in FIGS. 1 to 3.

As the experimental result, it was seen that, compared with a control only treated with UV irradiation, in the group treated with LTP before and after the UV treatment, the expression of pERK, p-p38, p-NFκB and p-EGFR decreases. NF-kB is known as a transcription factor causing the expression of a tumor necrosis factor (TNF) or an interleukin-6 (IL-6) molecule, which is involved in an immune response or inflammatory response by activating a gene expression system causing inflammation. Therefore, compared to a control not treated with LTP, in cells treated with LTP before and after UV damage, it can be understood that the reduced phosphorylation of ERK, p38 and EGFR as well as NF-kB is an effect of reducing the inflammatory response caused by skin damage.

Figure 4:
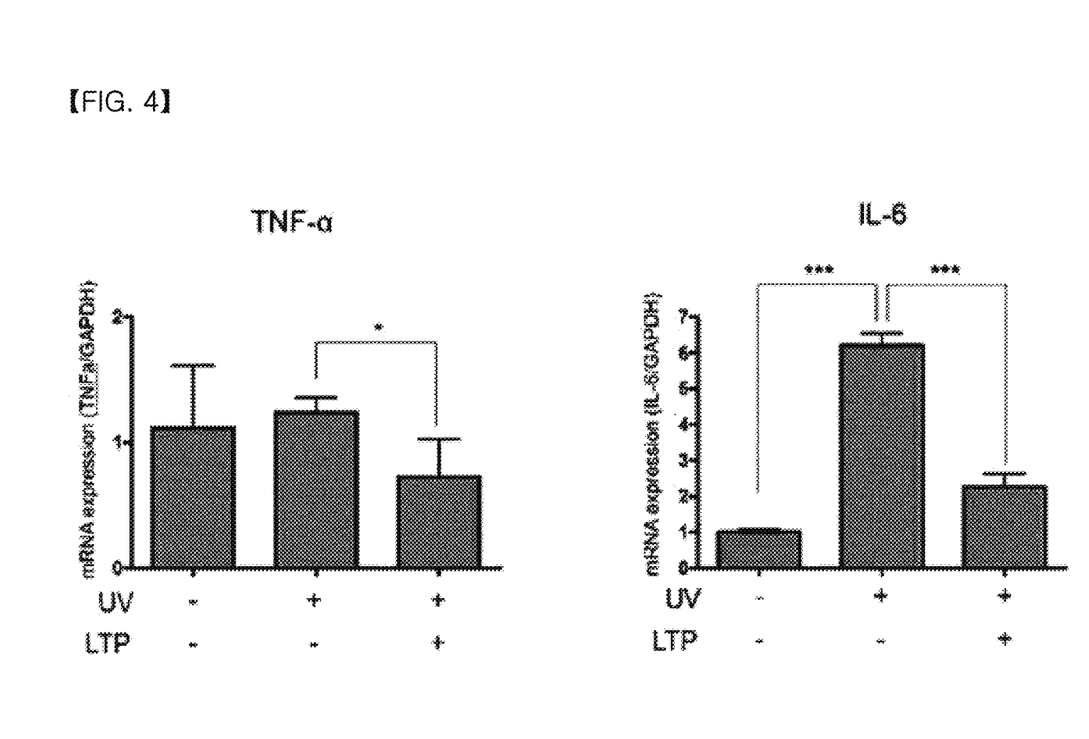
FIG. 4 shows the result of confirming the expression levels of INF-$\alpha$ and IL-6 in epidermal cells treated with LTP before and after UV stimulation according to an example of the present invention.

In addition, the expression levels of the TNF-α and IL-6 genes of the cells further cultured for 4 hours after the treatment with 20 mJ/cm$^2$ UV rays were confirmed by qPCR. TNF-α and IL-6 are known to be associated with the etiological cause of inflammation. Primer sets of TNF-α, IL-6 and GAPDH used herein were commercially available (Qiagen, Hilden, Germany), and expression levels were recalculated based on GAPDH signals of TNF-α and IL-6. The results are shown in FIG. 4.

As the experimental result, compared to the control only treated with UV irradiation, in the group treated with LTP before and after UV treatment, it was confirmed that the TNF-α and IL-6 expression was significantly reduced.

Example 4

Confirmation of LTP (Argon Plasma) Effect on UV-Damaged Epidermal Cells

Figure 5:
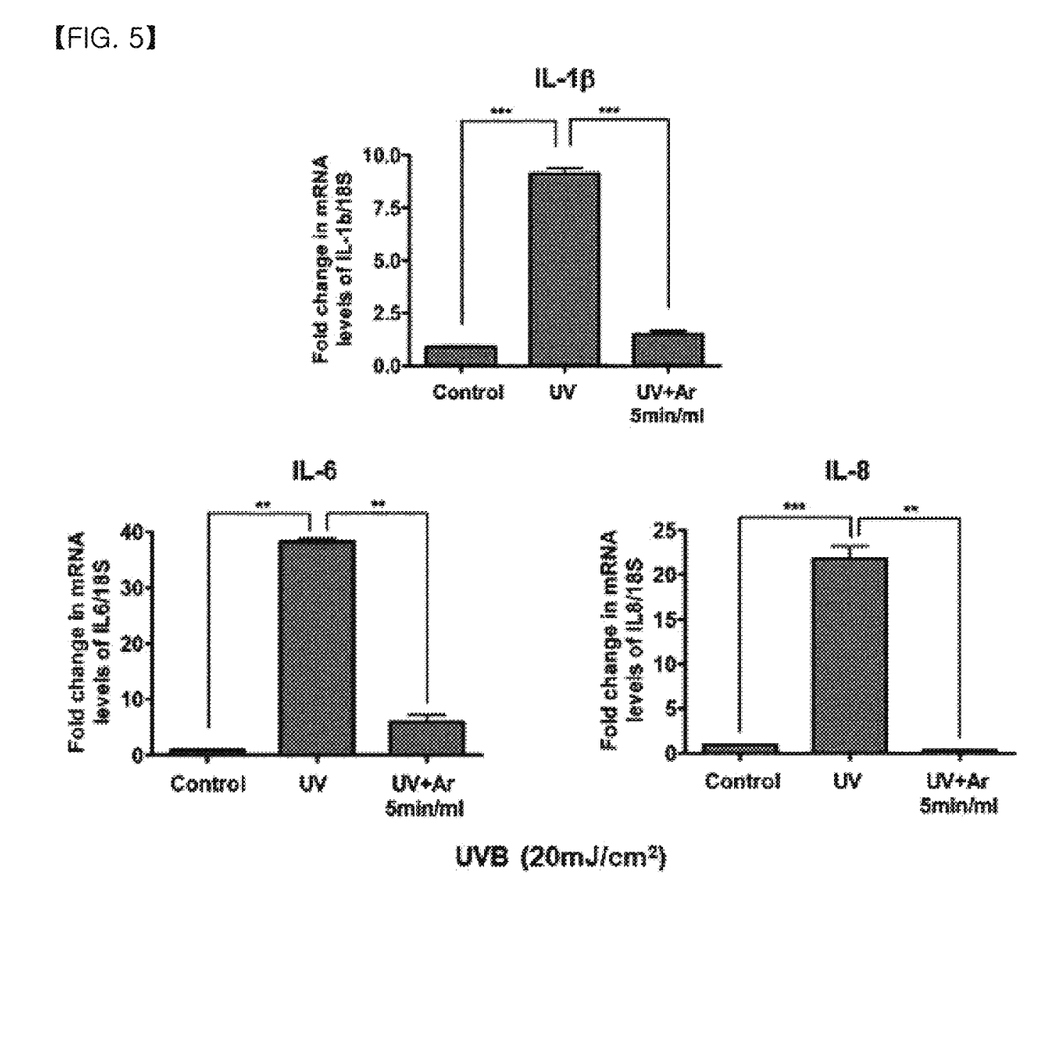
FIG. 5 shows the result of confirming the expression levels of IL-1$\beta$, IL-6 and IL-8 in epidermal cells treated with LTP (argon plasma) before and after UV stimulation according to an example of the present invention.

LTP was prepared by applying the same method as described in Example 1, except argon was supplied as a carrier gas, and an effect on UV-damaged epidermal cells was analyzed. FIG. 5 shows the result of confirming IL-1β, IL-6 and IL-8 expression levels in epidermal cells (HaCaT cells) treated with LTP (argon plasma) before and after UV irradiation through qPCR. To investigate an expression level of a transcriptome, the expression levels of the IL-1β, IL-6 and IL-8 genes of the epidermal cells treated with 20 mJ/cm$^2$ UV rays and then further cultured for 4 hours were confirmed by qPCR. Primer sets of IL-1β, IL-6, IL-8 and GAPDH were commercially available (Qiagen, Hilden, Germany), and the expression levels of IL-1β, IL-8 and IL-6 were recalculated based on a 18 s RNA level. As the experimental result, compared with a group only treated with UV treatment, in the group treated with argon plasma before and after UV irradiation (UVB, 20 mJ/cm$^2$), it was confirmed that the IL-1β, IL-6 and IL-8 expression corresponding to a proinflammatory cytokine was significantly reduced.

Figure 6:
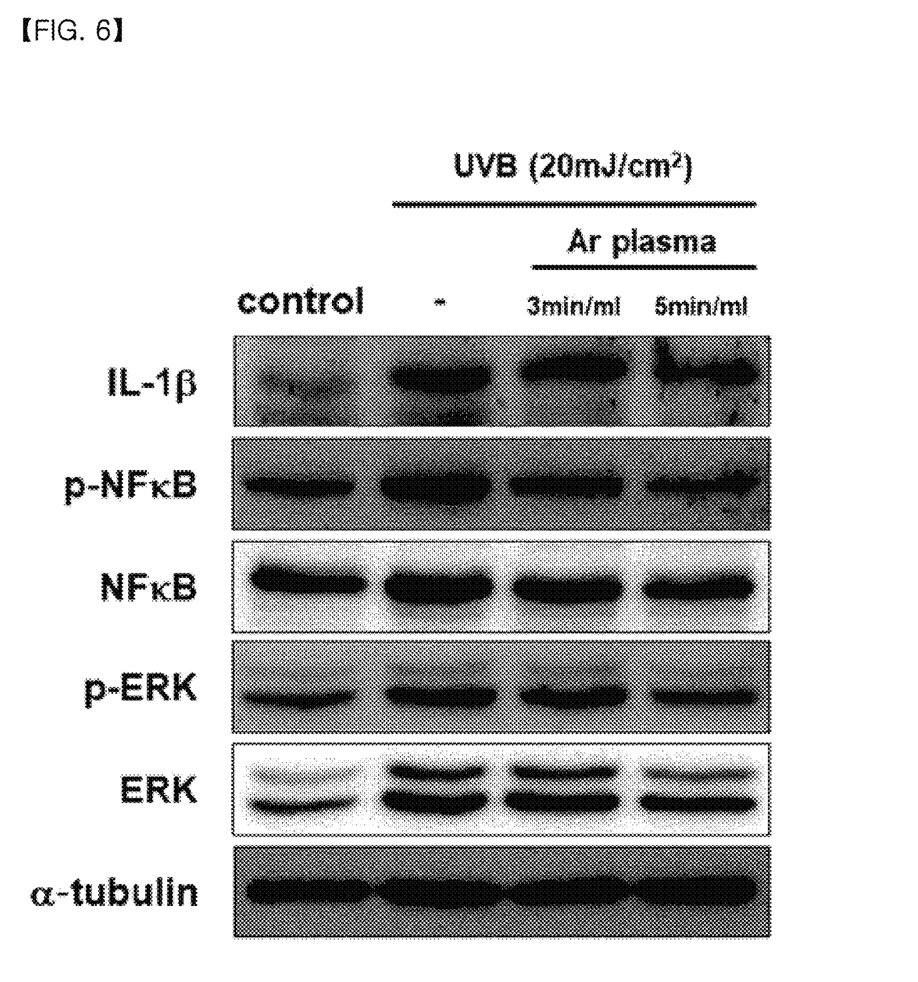
FIG. 6 shows the result of confirming the activity of p-NFkB, p-ERK and IL-1$\beta$ in epidermal cells treated with LTP (argon plasma) before and after UV stimulation according to an example of the present invention.

FIG. 6 shows the result of confirming the p-NFkB, p-ERK and IL-1β activity in epidermal cells treated with LTP (argon plasma) before and after UV irradiation (HaCaT cells). In this experiment, cells further incubated for 15 minutes or 4 hours (IL-1β) after treatment with 20 mJ/cm$^2$ UN rays were lysed with an RIPA buffer (150 mM NaCl, 1.0% Nonidet-P 40, 0.5% sodium deoxycholate, 0.1% sodium dodecyl sulfate, 50 mM Tris, pH 8.0, and a protease inhibitor cocktail, and PhoSTOP (Roche Molecular Biochemicals, Basel, Switzerland)), 10 µg of a protein lysate was loaded in a 10% SDS/PAGE gel to isolate proteins, and the proteins were transferred to a PVDF membrane (Amersham, Arlington Heights, Ill., USA). A pERK, ERK, p-p38, p38, p-NFκB, NFκB, p-EGFR, EGFR, or GAPDH (Cell Signaling Technology) antibody was reacted with the protein-transferred. PVDF membrane, and the extent of the expression of each signal was measured with ECL Western blotting detection reagents (Amersham). The expression level of each signal was recalculated based on a GAPDH signal. As the experimental result, it was confirmed that, compared with the group only treated with UV rays, in the group treated with an argon plasma before and after UV irradiation (UVB, 20 mJ/cm$^2$), in epidermal cells treated with LTP (argon plasma) before and after the UV irradiation (UVB, 20 mJ/cm$^2$), the activity of p-NF-kB and p-ERK corresponding to skin inflammatory molecules is reduced, and the production of IL-1β corresponding to a proinflammatory cytokine is reduced.

From the results of FIGS. 1 to 6, it was seen that the LTP treatment of the skin before and after UV damage has a significant effect on the prevention or treatment of dermatitis or photoaging caused by UV rays.

The invention claimed is:
1. A cosmetic composition for soothing skin, comprising a plasma-conditioned liquid material prepared by a method comprising:
   (a) filling a plasma generator with a carrier gas;

(b) generating a plasma by providing a voltage of 1 kV to 30 kV and a frequency of 10 to 30 kHz to the plasma generator; and
(c) irradiating a liquid-phase material with the generated plasma, as an active ingredient.

2. A cosmetic composition for preventing or improving photoaging, comprising a plasma-conditioned liquid material prepared by a method comprising:
(a) filling a plasma generator with a carrier gas;
(b) generating a plasma by providing a voltage of 1 kV to 30 kV and a frequency of 10 to 30 kHz to the plasma generator; and
(c) irradiating a liquid-phase material with the generated plasma, as an active ingredient.

\* \* \* \* \*